US012005143B2

(12) United States Patent
Sugiyama et al.

(10) Patent No.: US 12,005,143 B2
(45) Date of Patent: Jun. 11, 2024

(54) METHOD FOR PRODUCING LIPOSOME AND APPARATUS FOR PRODUCING LIPOSOME

(71) Applicant: FUJIFILM Corporation, Tokyo (JP)

(72) Inventors: Susumu Sugiyama, Kanagawa (JP); Naoki Yamada, Kanagawa (JP); Shigehisa Sugiyama, Kanagawa (JP); Yohei Okubo, Minami-ashigara (JP)

(73) Assignee: FUJIFILM Corporation, Tokyo (JP)

( * ) Notice: Subject to any disclaimer, the term of this patent is extended or adjusted under 35 U.S.C. 154(b) by 346 days.

(21) Appl. No.: 15/868,160

(22) Filed: Jan. 11, 2018

(65) Prior Publication Data

US 2018/0133156 A1 May 17, 2018

Related U.S. Application Data

(60) Division of application No. 15/625,391, filed on Jun. 16, 2017, now Pat. No. 10,485,760, which is a
(Continued)

(30) Foreign Application Priority Data

Dec. 19, 2014 (JP) .................................. 2014-257282

(51) Int. Cl.
*A61K 9/127* (2006.01)
*A61K 31/7068* (2006.01)
(Continued)

(52) U.S. Cl.
CPC ............ *A61K 9/1277* (2013.01); *A61K 9/127* (2013.01); *A61K 9/1271* (2013.01);
(Continued)

(58) Field of Classification Search
CPC ..................................................... A61K 9/1277
(Continued)

(56) References Cited

U.S. PATENT DOCUMENTS

| 4,551,288 A | 11/1985 | Kelly |
| 4,752,425 A | 6/1988 | Martin et al. |

(Continued)

FOREIGN PATENT DOCUMENTS

| JP | 7-328620 A | 12/1995 |
| JP | 2000-27024 A | 1/2000 |

(Continued)

OTHER PUBLICATIONS

Charles Ross and Son Company. Ross In-Line Series 700 Mixer Specifications and Dimensions. Feb. 27, 2012. WayBack Machine screenshot <https://web.archive.org/web/20120227055543/https://www.mixers.com/Specifications/Series700.pdf>. Retrieved Dec. 24, 2017 (Year: 2012).

(Continued)

*Primary Examiner* — Marc C Howell
(74) *Attorney, Agent, or Firm* — Birch, Stewart, Kolasch & Birch, LLP

(57) ABSTRACT

Disclosed herein are a method for producing a miniaturized liposome on a large production scale, and an apparatus for producing a liposome which is to be used in the above-mentioned method. Provided is a method for producing a liposome, including a step of stirring a mixture containing an oil phase in which at least one lipid is dissolved in an organic solvent and a water phase in a first tank of an apparatus having the first tank and a circulation path, in which the ratio of the capacity of the circulation path to the total capacity of the tank and the circulation path is 0.4 or less and/or the time required for the mixture to return to the first tank after being discharged therefrom is within 2.0 minutes.

11 Claims, 1 Drawing Sheet

Related U.S. Application Data continuation of application No. PCT/JP2015/085455, filed on Dec. 18, 2015.

(51) Int. Cl.

| | | |
|---|---|---|
| *B01F 23/40* | (2022.01) | |
| *B01F 23/41* | (2022.01) | |
| *B01F 25/21* | (2022.01) | |
| *B01F 25/50* | (2022.01) | |
| *B01J 13/04* | (2006.01) | |
| *B01J 13/08* | (2006.01) | |
| *B82Y 5/00* | (2011.01) | |
| *B82Y 40/00* | (2011.01) | |
| *B01F 101/22* | (2022.01) | |

(52) U.S. Cl.
CPC .......... *A61K 31/7068* (2013.01); *B01F 23/40* (2022.01); *B01F 23/41* (2022.01); *B01F 25/21* (2022.01); *B01F 25/50* (2022.01); *B01J 13/04* (2013.01); *B01J 13/08* (2013.01); *B82Y 5/00* (2013.01); *B82Y 40/00* (2013.01); *B01F 2101/22* (2022.01)

(58) Field of Classification Search
USPC ....................................................... 366/136
See application file for complete search history.

(56) References Cited

U.S. PATENT DOCUMENTS

| | | | |
|---|---|---|---|
| 4,781,871 A | 11/1988 | West et al. | |
| 5,000,887 A | 3/1991 | Tenzel et al. | |
| 5,194,188 A * | 3/1993 | Guitierrez | A61K 9/1277 264/4.1 |
| 5,469,854 A | 11/1995 | Unger et al. | |
| 5,554,382 A | 9/1996 | Castor | |
| 5,653,996 A | 8/1997 | Hsu | |
| 5,702,722 A | 12/1997 | Tournier et al. | |
| 5,716,526 A | 2/1998 | Kelemen et al. | |
| 5,776,486 A | 7/1998 | Castor et al. | |
| 6,217,899 B1 | 4/2001 | Benameur et al. | |
| 6,534,018 B1 | 3/2003 | Baker et al. | |
| 6,623,671 B2 | 9/2003 | Coe et al. | |
| 6,855,296 B1 | 2/2005 | Baker et al. | |
| 8,354,064 B2 | 1/2013 | Nakamura et al. | |
| 2003/0215515 A1 | 11/2003 | Truong-Le et al. | |
| 2007/0182040 A1 | 8/2007 | Suzuki et al. | |
| 2010/0112042 A1* | 5/2010 | Polisky | A61K 9/1271 514/1.1 |
| 2011/0024929 A1 | 2/2011 | Nakamura et al. | |
| 2011/0250264 A1 | 10/2011 | Schutt et al. | |

FOREIGN PATENT DOCUMENTS

| | | |
|---|---|---|
| JP | 2003-113596 A | 4/2003 |
| JP | 2006-512102 A | 4/2006 |
| JP | 2006-297360 A | 11/2006 |
| JP | 2008-302264 A | 12/2008 |
| JP | 2009-240954 A | 10/2009 |

OTHER PUBLICATIONS

GlobalSpec. Peristaltic Pumps Information. Aug. 30, 2012. WayBack Machine screenshot <https://web.archive.org/web/20120830061628/http://www.globalspec.com:80/learnmore/flow_transfer_control/pumps/peristaltic_pumps>. p. 1-4. Retrieved Dec. 24, 2017 (Year:2012).
International Preliminary Report on Patentability for PCT/JP2015/085455 (PCT/IPEA/409) with transmittal (PCT/IPEA/416) completed on Jul. 29, 2016.
International Search Report for PCT/JP2015/085455 (PCT/ISA/210) mailed on Feb. 16, 2016.
Notification of Transmittal of Translation of the International Preliminary Report on Patentability, English Translation of the International Preliminary Report on Patentability, dated Jun. 22, 2017, issued in PCT/JP2015/085455 (Forms PCT/IB/338 and PCT/IPEA/409).
Office Action issued Dec. 28, 2017 in U.S. Appl. No. 15/625,391.
ResearchGate Scientific Professionals. "How can I reduce the vesicle size of liposomes?" 2014. ResearchGate.net. Pg 1-4. < https://www.researchgate.net/post/How_can_I_reduce_the_vesicle_size_of_liposomes_below_100_nm_by_high_pressure_homogenizer_above_phase_transition_temperature>. Retrieved Dec. 25, 2017 (Year: 2014).
Written Opinion of the International Searching Authority for PCT/JP2015/085455 (PCT/ISA/237) mailed on Feb. 16, 2016.
Japanese Office Action, dated Dec. 26, 2017, for corresponding Japanese Application No. 2014-257282, with an English machine translation.
U.S. Office Action for parent U.S. Appl. No. 15/625,391, dated Jul. 20, 2018.

* cited by examiner

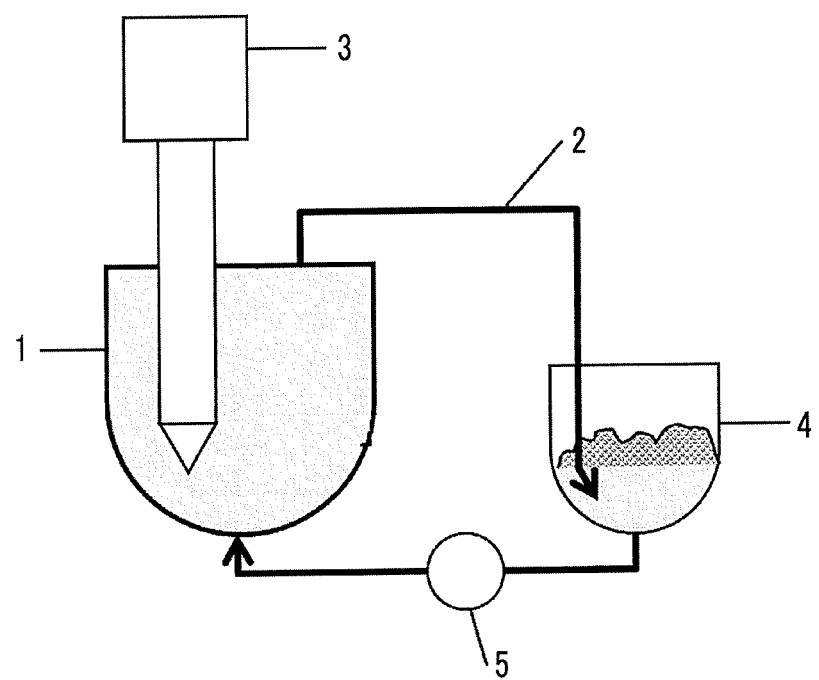

METHOD FOR PRODUCING LIPOSOME AND APPARATUS FOR PRODUCING LIPOSOME

CROSS-REFERENCE TO RELATED APPLICATIONS

The present application is a division of co-pending U.S. patent application Ser. No. 15/625,391 filed Jun. 16, 2017, which is a continuation of PCT International Application PCT/JP2015/085455 filed on Dec. 18, 2015, which claims priority under 35 U.S.C. § 119 of Japanese Patent Application No. 257282/2014 filed on Dec. 19, 2014, all of which are hereby expressly incorporated by reference into the present application.

BACKGROUND OF THE INVENTION

1. Field of the Invention

The present invention relates to a method for producing a liposome and an apparatus for producing a liposome. Specifically, the present invention relates to a method for producing a liposome which can be suitably used for pharmaceutical applications, and an apparatus for producing such a liposome.

2. Description of the Related Art

A liposome (hereinafter, also referred to as lipid vesicle) is a closed vesicle formed of a lipid bilayer membrane using lipids, and has an aqueous solution (outer water phase) in which liposomes are dispersed and a water phase (inner water phase) within the space of the closed vesicle. Liposomes have been studied for a variety of applications such as immune sensors, artificial red blood cells, and carriers of drug delivery systems taking advantage of the features such as barrier capacity, compound retention capacity, biocompatibility, the degree of freedom of setting the particle size, ready biodegradability, and surface-modifying properties. As for the application of a carrier, liposomes can encapsulate water-soluble compounds, lipophilic low-molecular weight and high-molecular weight materials, and a wide range of materials. In particular, in the case where the liposome is used as a carrier for a drug delivery system, the particle size of the liposome is preferably small from the viewpoint of permeability in biological membranes.

Liposomes can be prepared by stirring and emulsifying a water phase and an oil phase in a stirring apparatus. Since foaming may occur during the emulsification in a stirring apparatus, it is preferable to have a defoaming means.

With regard to the defoaming means, for example, JP2008-302264A discloses a defoaming tank including a tank body for containing a liquid to be treated in a state in which a liquid surface is vertically variable and a plurality of defoaming nozzles for diffusing and ejecting a defoaming liquid from above the liquid to be treated, in which bubbles contained in the liquid to be treated are defoamed by spraying the defoaming liquid from the plurality of defoaming nozzles toward the liquid surface of the liquid to be treated. It is also described that this defoaming tank is used in connection with a floating concentration column 6, which is an example of a solids floating apparatus. JP2006-297360A discloses a liquid circulation type reduced pressure concentration apparatus consisting of a preheating reservoir tank for a foamable liquid, a defoaming machine and a condenser, which is configured to prevent foaming in such a way that a rotating body is placed in the defoaming machine, the foamable liquid preheated in the preheating reservoir tank is fed into the rotating body of the defoaming machine, and the liquid droplets are finely dispersed into fine particles and released from the rotating body. JP1995-328620A (JP-H07-328620A) discloses a centrifugal sedimentation type centrifuge apparatus for removing a solid from a mixture containing a liquid and a solid having a specific gravity smaller than that of the liquid, which is characterized by providing a rotor having an inside disc. It is also stated that a defoaming tank is provided. JP2000-027024A discloses an oil agent defoaming apparatus formed by connecting an oil agent tank and an oil agent application device to an oil agent delivery pipe and an oil agent return pipe, characterized in that a suction device having a suction port for sucking bubbles in the oil agent tank is provided such that the distance between the oil agent liquid surface in the oil agent tank and the suction port is 50 to 110 mm. JP2003-113596A discloses a defoaming apparatus having a function of sucking bubbles from a liquid surface and breaking the bubbles by a centrifugal force of a rotating body and then returning the swollen liquid back to the liquid surface.

SUMMARY OF THE INVENTION

It has been attempted to reduce the loss of emulsification energy due to foaming by providing a defoaming tank. Since emulsified oil droplets and dispersions are usually stable and do not undergo re-coalescence within a short period of time, a known combination of an emulsifying tank and a defoaming tank is configured to have a structure in which the size of the emulsifying tank is fixed to a minimum and the external tank is enlarged from the viewpoint of a scale-up suitability. That is, the capacity of the defoaming tank becomes larger than the capacity of the emulsifying tank. However, in the method for producing a liposome including a step of stirring a mixture containing an oil phase and a water phase, there is a problem that it is not possible to achieve the desired miniaturization even if the emulsification time is prolonged because re-coalescence may occur due to retention in the emulsifying tank.

In addition, the circulating flow rate between an emulsifying tank and a defoaming tank has not particularly been considered because the emulsified oil droplets and dispersions as described above are stable in general emulsions. However, in the emulsification of liposomes, if the circulation flow rate is small, the re-coalescence proceeds corresponding to the amount of the residence time in the circulation path and therefore it has not been possible to achieve miniaturization beyond a certain level.

As described above, in the preparation of liposomes by an emulsification method, until the solvent has been removed after emulsification, the miniaturized dispersion becomes an unstable equilibrium system in which the particle size is increased due to re-coalescence. Therefore, in the case where the production scale becomes larger, only by simply extending the emulsification time, miniaturization is limited to a certain particle size, and it cannot be further miniaturized. In order to achieve a predetermined miniaturization, it is necessary to increase the energy per unit volume of the liquid supplied by an emulsifying apparatus. However, if the size of the emulsifying apparatus is simply enlarged to increase the output, air entrainment becomes severe, and therefore most of the shearing energy is wasted due to shearing of air resulting in foaming, and consequently it is not possible to achieve a predetermined particle size.

It is an object of the present invention to provide a method for producing a miniaturized liposome on large scale production, and an apparatus for producing a liposome which is to be used in the above-mentioned method.

As a result of extensive studies to solve the above-mentioned problems, the present inventors have found that, in a method for producing a liposome, including a step of stirring a mixture containing an oil phase and a water phase in a first tank of an apparatus having the first tank and a circulation path, it is capable of producing miniaturized liposomes on a large production scale, by setting the ratio of the capacity of the circulation path to the total capacity of the tank and the circulation path to be 0.4 or less and/or setting the time required for the mixture to return to the first tank after being discharged therefrom to be within 2.0 minutes. The present invention has been completed based on such findings. That is, according to the present invention, the following will be provided.

(1) A method for producing a liposome, comprising a step of stirring a mixture containing an oil phase in which at least one lipid is dissolved in an organic solvent and a water phase in a first tank of an apparatus having the first tank and a circulation path, in which the ratio of the capacity of the circulation path to the total capacity of the tank and the circulation path is 0.4 or less and/or the time required for the mixture to return to the first tank after being discharged therefrom is within 2.0 minutes.

(2) The method for producing a liposome according to (1), in which the apparatus has a second tank in the middle of the circulation path.

(3) The method for producing a liposome according to (2), in which the inside of the second tank has saturated vapor.

(4) The method for producing a liposome according to any one of (1) to (3), in which the first tank is filled with the mixture.

(5) The method for producing a liposome according to any one of (1) to (4), in which the mixture in the first tank is subjected to a pressure load.

(6) The method for producing a liposome according to any one of (1) to (5), in which the mixture is circulated in the first tank and the circulation path using a diaphragm pump or a rotary pump.

(7) The method for producing a liposome according to any one of (1) to (6), in which the mixture is stirred in the first tank using an intermittent jet flow generating type emulsifying apparatus.

(8) The method for producing a liposome according to any one of (1) to (7), in which the lipid includes a polyethylene glycol-modified lipid.

(9) The method for producing a liposome according to any one of (1) to (8), in which the average particle size of the liposomes to be produced is 60 nm or less.

(10) The method for producing a liposome according to any one of (1) to (9), in which the capacity of the first tank is 10 L or more and 100 L or less.

(11) The method for producing a liposome according to any one of (1) to (10), in which the ratio of the capacity of the circulation path to the total capacity of the tank and the circulation path is 0.4 or less and the time required for the mixture to return to the first tank after being discharged therefrom is within 2.0 minutes.

(12) An apparatus for producing a liposome, comprising a first tank and a circulation path, in which the ratio of the capacity of the circulation path to the total capacity of the tank and the circulation path is 0.4 or less.

(13) The apparatus for producing a liposome according to (12), further comprising a second tank in the middle of the circulation path.

(14) The apparatus for producing a liposome according to (12) or (13), further comprising a pump in the middle of the circulation path.

(15) The apparatus for producing a liposome according to any one of (12) to (14), in which the pump is a diaphragm pump or a rotary pump.

(16) The apparatus for producing a liposome according to any one of (12) to (15), in which an intermittent jet flow generating type emulsifying apparatus is installed in the first tank.

According to the present invention, it is possible to produce a miniaturized liposome on a large production scale.

BRIEF DESCRIPTION OF THE DRAWINGS

FIG. 1 shows a configuration example of an apparatus for producing a liposome according to the present invention.

DESCRIPTION OF THE PREFERRED EMBODIMENTS

The term "step" used herein includes not only an independent step, but also a step which may not be clearly separated from another step, insofar as an expected effect of the step can be attained.

The numerical ranges shown with "to" in the present specification means ranges including the numerical values indicated before and after "to" as the minimum and maximum values, respectively.

In referring herein to a content of a component in a composition, in a case where plural substances exist corresponding to a component in the composition, the content means, the total amount of the plural substances existing within the composition, unless otherwise specified.

The present invention will be described in detail.

The method for producing a liposome according to the present invention is a method for producing a liposome, including a step of stirring a mixture containing an oil phase in which at least one lipid is dissolved in an organic solvent and a water phase in a first tank of an apparatus having the first tank and a circulation path, in which the ratio of the capacity of the circulation path to the total capacity of the tank and the circulation path is 0.4 or less and/or the time required for the mixture to return to the first tank after being discharged therefrom is within 2.0 minutes.

In the present invention, it is possible to efficiently use the energy of the emulsifying apparatus for miniaturization of the liposomes, by providing a circulation path preferably including a second tank (defoaming tank) outside the first tank (emulsifying tank) to thereby suppress the energy loss due to the shearing of air. Further, it is possible to achieve the desired miniaturization since re-coalescence of the liposomes due to the residence can be suppressed by setting the ratio of the capacity of the circulation path to the total capacity of the first tank and the circulation path to be 0.4 or less and/or the re-coalescence of liposomes can be suppressed by setting the time required for the mixture to return to the first tank after being discharged therefrom to be within 2.0 minutes. From the viewpoint of the specificity of liposomes that exist in an equilibrium system of dispersion and re-coalescence, being capable of producing fine liposomes by producing liposomes under the above-mentioned conditions, particularly in the case where the production scale is large, is a completely unexpected advantageous effect.

(Liposome)

Liposome is a lipid vesicle formed from a lipid bilayer containing lipid molecules. Specifically, the liposome refers to a vesicle containing a closed lipid having a space separated from the external environment by a lipid bilayer formed based on the polarity of the hydrophobic groups and hydrophilic groups of the lipid molecules. The liposome is a closed vesicle formed of a lipid bilayer membrane using lipids, and has a water phase (inner water phase) within the space of the closed vesicle. The inner water phase contains water and the like. The liposome may be single lamellar (monolayer lamellar, unilamellar, or single bilayer membrane) or multilayered lamellar (multilamellar, which is an onion-like structure having multiple bilayer membranes where individual layers are compartmented by water-like layers). In the present invention, a monolayer lamellar liposome is preferred from the viewpoint of safety and stability in pharmaceutical applications.

The liposome is preferably a liposome capable of encapsulating a drug and is not particularly limited in terms of form. The "encapsulating" means taking a form in which a drug is contained in an inner water phase and a membrane with respect to the liposome. For example, the liposome may be a form where a drug is encapsulated within a closed space formed of a membrane, a form where a drug is included in the membrane itself, or a combination thereof.

The size (average particle size) of the liposome is not particularly limited and is preferably 100 nm or less, more preferably 30 to 70 nm, still more preferably 40 to 60 nm, and particularly preferably 40 to 55 nm. The liposome is preferably in the form of a spherical shape or a shape close thereto. In the present invention, the "average particle size" means a volume average value of the diameters of liposomes as measured by a dynamic light scattering method.

The component (membrane component) constituting the lipid bilayer of a liposome is selected from lipids. As the lipid, any one may be used as long as it is dissolved in a mixed solvent of a water-soluble organic solvent and an ester-based organic solvent. Specific examples of lipids include phospholipids, lipids other than phospholipids, cholesterols and derivatives thereof. These components may be composed of single or plural components.

Examples of the phospholipid include natural or synthetic phospholipids such as phosphatidylcholine (lecithin), phosphatidyl glycerol, phosphatidic acid, phosphatidylethanolamine, phosphatidyl serine, phosphatidyl inositol, sphingomyelin, and cardiolipin, or hydrogenated products thereof (for example, hydrogenated soybean phosphatidylcholine (HSPC)). Among these, preferred is a hydrogenated phospholipid such as hydrogenated soybean phosphatidylcholine, or sphingomyelin, and more preferred is hydrogenated soybean phosphatidylcholine. In the present invention, the "phospholipid" also encompasses a phospholipid derivative in which the phospholipid is modified.

Lipids other than phospholipids may be lipids containing no phosphoric acid, and examples thereof include, but are not particularly limited to, glycerolipid which does not contain a phosphoric acid moiety within the molecule, and sphingolipid which does not contain a phosphoric acid moiety within the molecule. In the present invention, the term "lipids other than phospholipids" also encompasses derivatives of lipids other than phospholipids in which modifications have been made to the lipids other than phospholipids.

In the case where the lipids other than phospholipids contain a basic functional group, for example, in the case where the lipids other than phospholipids are a material where a compound having a basic functional group is bonded to a lipid, the lipid is referred to as a cationized lipid. The cationized lipid becomes capable of modifying, for example, the membrane of the liposome and therefore can enhance the adhesiveness to cells which are the target sites.

Examples of cholesterols include cholesterol which contains cyclopentahydrophenanthrene as a basic skeleton whose carbon atoms are partially or completely hydrogenated and derivatives thereof. Specific examples of cholesterols include, but are not particularly limited to, cholesterol. When the average particle size decreases to 100 nm or less, the curvature of the lipid membrane becomes higher. Since the deformation of the membrane arranged within the liposome also increases, a water-soluble drug becomes more susceptible to leakage. However, as a means for suppressing leakage properties, it is effective to add cholesterol or the like in order to fill the deformation of the membrane caused by the lipid (membrane-stabilizing effect).

The addition of cholesterol into liposome compositions is expected to lower the fluidity of the liposome membrane by filling membrane gaps of liposomes, or the like. Generally, it has been desired that the content of cholesterol in liposomes is usually an amount of up to about 50 mol % of the total moles of lipid components (total lipid).

In the present invention, in total moles of lipid components in the liposome composition (total lipid contained in the liposome composition), the content of cholesterol is preferably 10 to 35 mol %, more preferably 15 to 25 mol %, and still more preferably 17 to 21 mol %.

In addition to the above-mentioned components, a hydrophilic polymer or the like for improving retentivity in blood, fatty acid, diacetyl phosphate or the like as a membrane structure stabilizer, or α-tocopherol or the like as an antioxidant may be added to the liposome. In the present invention, it is preferable not to use additives such as a dispersing aid not approved for use as an intravenous injection in pharmaceutical applications, for example, a surfactant or the like.

The liposome preferably contains hydrophilic polymer-modified products of phospholipids, lipids other than phospholipids, or cholesterols as phospholipids, lipids other than phospholipids, cholesterols and derivatives thereof.

Examples of the hydrophilic polymer include, but are not particularly limited to, polyethylene glycols, polyglycerols, polypropylene glycols, polyvinyl alcohols, a styrene-maleic anhydride alternating copolymer, polyvinylpyrrolidone, and synthetic polyamino acid. The above-mentioned hydrophilic polymers may be used alone or in combination of two or more thereof.

Among these, from the viewpoint of retentivity in blood of a formulation, preferred are polyethylene glycols, polyglycerols, and polypropylene glycols, and more preferred are polyethylene glycol (PEG), polyglycerol (PG), and polypropylene glycol (PPG). Polyethylene glycol (PEG) is most commonly used and is preferable due to having an effect of improving the retentivity in blood.

The molecular weight of PEG is not particularly limited. The molecular weight of PEG is 500 to 10,000 daltons, preferably 1,000 to 7,000 daltons, and more preferably 2,000 to 5,000 daltons.

In the liposome, it is preferable to use a lipid modified by PEG (PEG-modified lipid), together with the main lipid contained in the liposome. Specific examples of the PEG-modified lipid include 1,2-distearoyl-3-phosphatidylethanolamine-PEG (DSPE-PEG; manufactured by Nippon Oil & Fats Co., Ltd.; specifically 1,2-distearoyl-3-phosphatidylethanolamine-PEG2000, or 1,2-distearoyl-3-phosphatidylethanolamine-PEG5000 is preferable) and distearoyl glycerol-PEG2000 (manufactured by Nippon Oil & Fats Co., Ltd.). These PEG-modified lipids may be added in an amount of 0.3 to 50 mass %, preferably 0.5 to 30 mass %, and more preferably 1 to 20 mass % with respect to total lipid content.

In the liposome, preferred is a lipid combination of hydrogenated soybean phosphatidylcholine (a main lipid contained in the liposome) and 1,2-distearoyl-3-phosphatidylethanolamine-PEG (a lipid used in combination with the main lipid).

The liposome preferably does not contain an anionic polymer (polyanion). In the present invention, since it is possible to control the release ability by means of an osmotic pressure of an inner water phase, there are advantages in that general versatility is excellent, and drugs which can be used in liposomes are not limited.

(Method for Producing Liposome)

The method for producing a liposome according to the present invention is a method for producing a liposome, including a step of stirring a mixture containing an oil phase in which at least one lipid is dissolved in an organic solvent and a water phase in a first tank of an apparatus having the first tank and a circulation path, in which the ratio of the capacity of the circulation path to the total capacity of the tank and the circulation path is 0.4 or less and/or the time required for the mixture to return to the first tank after being discharged therefrom is within 2.0 minutes.

Particularly preferred is a case satisfying both the condition in which the ratio of the capacity of the circulation path to the total capacity of the tank and the circulation path is 0.4 or less, and the condition in which the time required for the mixture to return to the first tank after being discharged therefrom is within 2.0 minutes.

The method for producing a liposome may include other steps such as an evaporation step of evaporating the organic solvent used in the emulsifying step, if necessary.

The emulsifying step of emulsifying mixed lipids dissolved in an organic solvent to form a liposome, without a drying and solidifying step, is not limited as long as it is a step of emulsification, but it is preferably a step of applying a high shearing force and performing microparticulation in an emulsifying step including an organic solvent. If necessary, evaporation (desolvation) of the organic solvent used in the emulsifying step may be carried out to form a liposome.

(Oil Phase)

As the organic solvent serving as an oil phase, a mixed solvent of a water-soluble organic solvent and an ester-based organic solvent is used. In the present invention, it is preferred that an organic solvent such as chloroform, methylene chloride, hexane, or cyclohexane is not substantially used as the organic solvent, and it is more preferred that these organic solvents are not used at all.

The water-soluble organic solvent is not particularly limited, and it is preferably an organic solvent having a property that is spontaneously miscible with water. Specific examples of the water-soluble organic solvent include alcohols such as methanol, ethanol, n-propanol, isopropanol, n-butanol, isobutanol, and t-butanol; glycols such as glycerol, ethylene glycol, and propylene glycol; and polyalkylene glycols such as polyethylene glycol. Among these, preferred are alcohols. The alcohol is preferably at least one selected from ethanol, methanol, 2-propanol, or t-butanol, more preferably at least one selected from ethanol, 2-propanol, or t-butanol, and still more preferably ethanol.

The ester-based organic solvent is not particularly limited, and it is preferably an ester obtained from the reaction of organic acids and alcohols. Specifically, the ester-based organic solvent is preferably at least one selected from ethyl acetate, methyl acetate, isopropyl acetate, t-butyl acetate, or methyl propionate, more preferably ethyl acetate, isopropyl acetate, or methyl propionate, and still more preferably ethyl acetate.

The mixing ratio of water-soluble organic solvent:ester-based organic solvent is not particularly limited, and it may be about 90:10 to 20:80 and preferably about 70:30 to 25:75 by mass ratio. The mixed solvent of a water-soluble organic solvent and an ester-based organic solvent may further contain an aqueous solvent to be described below, such as water or buffer. The aqueous solvent may be added in a range of, for example, 1 to 30 mass %. The pH of the mixed solvent is not particularly limited, and it is in the range of preferably about 4 to 10 and more preferably about 6 to 9. The ester-based organic solvents may contain physiologically active substances or the like such as various drugs which are soluble in these solvents.

The concentration of the lipid is not particularly limited and may be appropriately adjusted, but it may be 40 g/L to 250 g/L, preferably 100 g/L to 200 g/L in terms of a solution where a mixed liquid of a water-soluble organic solvent and an ester-based organic solvent serves as a solvent.

(Water Phase)

As a water phase (aqueous solution) where the membrane components are dispersed when producing liposomes, water (distilled water, water for injection, or the like), physiological saline, various buffers, an aqueous solution of sugars or a mixture thereof (aqueous solvent) is preferably used. The buffer is not limited to organic and inorganic buffer solutions, and a buffer having a buffering action in the vicinity of a pH close to that of a body fluid is preferably used and examples thereof include phosphate buffer, Tris buffer, citrate buffer, acetate buffer, and Good's buffer. The pH of the water phase is not particularly limited, and it may be 5.0 to 9.0 and preferably 7.0 to 8.0. For example, a phosphate buffer (for example, pH=7.4) is preferably used. The aqueous solution finally contained in the inner water phase of the liposome may be an aqueous solution for dispersing the membrane components when producing the liposome, or may be water, physiological saline, various buffers, an aqueous solution of sugars or a mixture thereof which is newly added. The water used as a water phase (aqueous solution) is preferably free from impurities (dust, chemicals, or the like).

(Emulsifying Step)

In the emulsifying step, an oil phase where at least one lipid has been dissolved in an organic solvent and a water phase are mixed to prepare an aqueous solution containing lipids, which is then emulsified by stirring. An oil phase where lipids have been dissolved in an organic solvent and a water phase are mixed, stirred and emulsified to thereby prepare an emulsion where an oil phase and a water phase are emulsified in an O/W type. After mixing, a liposome is formed by removing a portion or all of the organic solvent derived from the oil phase using an evaporating step to be described below. Alternatively, a portion or all of the organic solvent in the oil phase is evaporated during the course of the stirring-emulsification to form a liposome.

As a method of stirring, ultrasonic waves or mechanical shearing force is used for particle miniaturization. A preferred emulsifying apparatus will be described later herein. In addition, extruder processing of allowing to pass through a filter having a certain pore size or microfluidizer processing may be carried out for uniformity of the particle sizes. Use of an extruder or the like can result in deformation of secondarily formed multivesicular liposomes into univesicular liposomes. In the present invention, it is preferred from the viewpoint of simplification of the production process that a liposome of a state that has no drug loading is used in the next step without extrusion processing.

In the present invention, the ratio of the capacity of the circulation path to the total capacity of the first tank and the circulation path is 0.4 or less and/or the time required for the mixture to return to the first tank after being discharged therefrom is within 2.0 minutes. The ratio of the capacity of the circulation path to the total capacity of the first tank and the circulation path is preferably 0.3 or less, more preferably 0.20 or less, and an example thereof is 0.19. The lower limit of the ratio of the capacity of the circulation path to the total capacity of the first tank and the circulation path is not particularly limited, but it is generally 0.10 or more.

The time required for the mixture to return to the first tank after being discharged therefrom is preferably within 1.0 minute, more preferably within 0.8 minutes, and still more preferably within 0.6 minutes. The lower limit of the foregoing time is not particularly limited, but it is generally 0.1 minutes or more from the viewpoint of the defoaming effects.

Emulsification is carried out by stirring in a first tank of an apparatus having the first tank and a circulation path. The capacity of the first tank is not particularly limited, but from the viewpoint of large scale production being favorable, it is preferably 10 L or more and 100 L or less and more preferably 20 L or more and 100 L or less.

Preferably, the first tank is filled with a mixture. By fully filling the emulsifying tank, the gas-liquid interface is eliminated, and the loss of energy due to foaming can be further suppressed. If a small amount of air remains in sight glass of the upper part of the first tank, or the like, the effect is not affected, and the emulsifying liquid part may be substantially filled with the mixture.

Preferably, the mixture in the first tank may be subjected to a pressure load. This makes it possible to further reduce the loss of energy due to foaming. The pressure load can be realized, for example, by providing a valve narrowing the flow path in the middle of the circulation path derived from the first tank.

In the present invention, a second tank for defoaming may be preferably provided in the middle of the circulation path. By providing the second tank, defoaming can be performed efficiently. In the case where the circulation path has the second tank, the above-mentioned capacity of the circulation path refers to the capacity of the entire circulation path including the second tank. In addition, it is preferable that the second tank has saturated vapor from the viewpoint of suppressing coarse materials being generated from skinning due to drying. Depending on the needs, such as stabilizing the circulating flow rate, the second tank may also be subjected to a pressure load. The pressure load may be achieved, for example, by introducing compressed air or compressed nitrogen into the second tank.

When carrying out the emulsification, it is preferred to have a mixture circulate in the first tank and the circulation path using a pump which may be a turbo-type pump (a centrifugal pump, a diagonal flow pump, or an axial flow pump), a positive displacement reciprocating pump (a piston pump, a plunger pump, or a diaphragm pump), a positive displacement rotary pump (a rotary pump, a gear pump, a vane pump, or a screw pump), a tube pump, or the like. Among them, a tube pump or a diaphragm pump having no sliding surfaces may be preferably used. It is also possible to preferably use a positive displacement rotary pump with a small pulsation of a circulating flow rate. Particularly preferred is a diaphragm pump or a rotary pump that can easily secure a large flow rate.

For emulsification, it is preferable to stir a mixture in the first tank using an emulsifying apparatus. Examples of the emulsifying apparatus that can be used include an impeller type, a sawtooth blade type, a closed rotor type, a rotor/stator type, a static mixer type, a colloid mill type, and a high-pressure homogenizer type. Among them, preferred is an impeller type, a sawtooth type, a closed rotor type, or a rotor/stator type which is suitable for batch processing in a tank.

Particularly preferred is a rotor/stator type which is capable of generating a jet flow in a treatment liquid by high-speed rotation for miniaturization, and capable of sufficiently exerting shear forces between liquid and liquid or liquid and wall surface. As an example, an intermittent jet flow generating type emulsifying apparatus can be used.

The intermittent jet flow generating type emulsifying apparatus is composed of a rotor and a screen, where the rotor rotates at a high speed while keeping minute clearance with the screen. The velocity of the processing material that has been given kinetic energy through the high-speed rotating rotor is increased by being passed through the slit portion of the screen. The processing material with an increased velocity forms an intermittent jet flow within the processing material in the tank and generates liquid-liquid shear forces at the velocity interface. It is possible to carry out atomization by the shear forces generated by this intermittent jet flow. The particle size and the particle size distribution can be controlled by the combination of a rotor and a screen.

In the present invention, an average particle size of a liposome to be prepared can be controlled by arbitrarily selecting the speed and time of stirring. In view of obtaining a liposome having safety and stability, it is preferable to provide shearing at a circumferential speed of 15 m/sec or higher to an aqueous solution containing lipids. Shearing is not limited, and a specific example thereof is shearing at a circumferential speed of preferably 15 m/sec or higher and 35 m/sec or lower, more preferably shearing at a circumferential speed of 20 m/sec or higher and 35 m/sec or lower, and still more preferably shearing at a circumferential speed of 23 m/sec or higher and 30 m/sec or lower.

(Apparatus for Producing Liposome)

The apparatus for producing a liposome according to the present invention includes a first tank and a circulation path, in which the ratio of the capacity of the circulation path to the total capacity of the tank and circulation path is 0.3 or less. The preferred range of the above-mentioned ratio is as described above in the present specification. Further, the preferred range of the capacity of the first tank is also as described above in the present specification.

An example of the configuration of the apparatus for producing a liposome according to the present invention is shown in FIG. 1.

A first tank 1, which is an emulsifying tank, is provided with a circulation path 2. The liquid in the first tank 1 is discharged from the first tank 1 and circulates through the circulation path 2 to return to the first tank 1. The first tank 1 is provided with an emulsifying apparatus 3. By operating the emulsifying apparatus 3, the liquid is stirred and emulsified in the first tank 1. In the middle of the circulation path 2, a second tank 4, which is a defoaming tank, and a pump 5 are provided. The bubbles can be separated and removed in the second tank 4. In addition, the liquid can be circulated in the circulation path by operating the pump 5. Further, the circulation flow rate can be controlled by adjusting the output of the pump.

(Evaporating Step)

In the present invention, an evaporating step may be provided if necessary. In the evaporating step, an organic solvent is evaporated from the aqueous solution containing the liposomes obtained in the emulsifying step. In the present invention, the evaporating step includes at least one of a step of forcibly removing a portion or all of the organic solvent derived from the oil phase as an evaporating step and a step of naturally evaporating a portion or all of the organic solvent in the oil phase during the course of stirring-emulsification.

The method of evaporating an organic solvent in the evaporating step is not particularly limited. For example, at least one of a step of heating to evaporate an organic solvent, a step of continuing the standing or slow stirring after emulsification, or a step of performing vacuum degassing may be carried out.

In the present invention, in the step of evaporating an organic solvent, it is preferred that the concentration of an organic solvent contained in an aqueous solution containing liposomes is to be 15 mass % or less within 30 minutes since the start of a step of evaporating the organic solvent.

A liquid temperature when carrying out the production method of the present invention can be appropriately adjusted, but the liquid temperature at the time of mixing an oil phase and a water phase is preferably higher than or equal to a phase transition temperature of the lipid to be used. For example, in the case where a lipid having a phase transition temperature of 35° C. to 40° C. is used, the liquid temperature is preferably set to 35° C. to 70° C.

The aqueous solution containing the liposomes prepared via an emulsifying step may be subjected to post-processing such as centrifugation, ultrafiltration, dialysis, gel filtration, or freeze-drying, for removal of components that had not been included in the liposomes, or adjustment of a concentration and an osmotic pressure.

Particle sizes of the resulting liposomes can be made uniform by using dialysis, filtration, extrusion processing, or the like. In the method for producing a liposome composition according to the present invention, it is preferred to prepare empty liposomes in a state where a drug is not loaded, without subjecting to extrusion processing. Moreover, if it is desired to separate the drug encapsulated in liposomes from the drug not encapsulated in liposomes, centrifugation, dialysis, gel filtration, or the like may be employed.

(Drug Loading Step)

The liposome obtained by the method of the present invention can encapsulate a drug. In the drug loading step of encapsulating the drug, in the case of encapsulating a water-soluble drug in the liposomes, the drug can be encapsulated in the inner water phase of the liposome by a method of dissolving the drug in an aqueous medium capable of performing hydration and swelling, followed by heating at a temperature higher than or equal to the phase transition temperature, and sonication or extrusion. A drug may also be encapsulated in an inner water phase by dissolving the drug in the water phase at a time of lipid emulsification.

The drug contained in the liposome may be any water-soluble drug that can be encapsulated in liposomes, and specific examples thereof include, but are not limited to, water-soluble materials having a physiological activity or a pharmacological activity such as enzymes, proteins, peptides, nucleic acids (DNA, mRNA, siRNA, miRNA), low-molecular weight compounds, sugars (oligosaccharides and polysaccharides), polymer compounds, antitumor agents, antimicrobial agents, contrast agents, antioxidants, anti-inflammatory agents, whitening agents, humectants, and hair growing agents. In the case of using a liposome as a carrier for a drug delivery system, the water-soluble drug is preferably a low-molecular weight compound from the viewpoint of stability.

Specific examples of the water-soluble drug include anti-cancer agents such as an anthracycline-based anticancer agent such as doxorubicin, daunorubicin or epirubicin, a cisplatin-based anticancer agent such as cisplatin or oxaliplatin, a taxane-based anticancer agent such as paclitaxel or docetaxel, a vinca alkaloid-based anticancer agent such as vincristine or vinblastine, a bleomycin-based anticancer agent such as bleomycin, a sirolimus-based anticancer agent such as sirolimus, and a metabolic antagonist such as methotrexate, fluorouracil, gemcitabine, cytarabine, or pemetrexed. Among these, preferred is a water-soluble drug such as doxorubicin, gemcitabine, or pemetrexed.

The water-soluble drug encapsulated in the liposome is present in a dissolved state in the inner water phase of the liposome. Here, with regard to the dissolved state, it is deemed to be encapsulated as a dissolved state in a case where the amount of the drug filled with respect to the volume of the liposome is below the saturation solubility of the drug in the composition liquid of the inner water phase. Further, even when the amount of the drug filled is above the saturation solubility of the drug, a case where drug crystals are not observed by a cryo-transmission electron microscope (Cryo-TEM) and diffraction patterns attributable to crystal lattice are not observed by X-ray diffraction (XRD) measurement indicates that most of the drug is dissolved due to acceleration of dissolution by a physicochemical environment created by the lipid membrane, partial incorporation of the drug into the lipid membrane or the like, and is deemed to be encapsulated as a dissolved state. In addition, a substance encapsulated by a loading method in which a solid substance is formed inside the liposome and a drug is encapsulated is not in a dissolved state, even when it is a highly water-soluble drug.

The water-soluble drug to be encapsulated in a dissolved state preferably has a solubility in water of 1 mg/ml or more, and more preferably a solubility in water of 10 mg/ml or more.

(Sterile Filtration)

In order to formulate an aqueous solution containing liposomes, obtained by the method for producing a liposome composition according to the present invention, into a pharmaceutical composition, it is preferable to carry out sterile filtration. Regarding the filtration method, it is possible to remove unwanted materials from the aqueous solution containing liposomes by using a hollow fiber membrane, a reverse osmosis membrane, a membrane filter or the like. In the present invention, the aqueous solution containing liposomes is preferably filtered using a filter having a sterile pore size (preferably 0.2 μm sterile filter) although there is no particular limitation. Normally, adsorption or aggregation of liposomes onto a sterile filter may occur in the filtration step. However, the present invention has unexpected effects such as little influence in pressure loss or the like when performing filtration, since liposomes having a specific average particle size and a uniform particle size distribution are obtained.

To prevent an effect of deformation of liposomes on the average particle size, the sterile filtration step and the below-described aseptic filling step are preferably carried out at a temperature lower than or equal to the phase transition temperature of the lipids constituting the liposome. For example, in the case where the phase transition temperature of the lipid is around 50° C., the sterile filtration step and the below-described aseptic filling step are carried out at a temperature of preferably about 0° C. to 40° C., and more specifically about 5° C. to 30° C.

(Aseptic Filling)

The aqueous solution containing the liposomes obtained after sterile filtration is preferably aseptically filled for medical applications. Known methods can be applied for aseptic filling. A liposome composition suitable for medical applications can be prepared by aseptically filling the liposome-containing aqueous solution in a container.

An aqueous solvent, an additive, or the like may be appropriately added to the aqueous solution containing the liposomes obtained by the present invention to thereby prepare a pharmaceutical composition containing liposomes. In connection with the route of administration, the pharmaceutical composition may also contain at least one of a tonicity agent, a stabilizer, an antioxidant, or a pH adjusting agent which is pharmaceutically acceptable.

The tonicity agent is not particularly limited and examples thereof include inorganic salts such as sodium chloride, potassium chloride, sodium hydrogen phosphate, sodium dihydrogen phosphate, and potassium dihydrogen phosphate; polyols such as glycerol, mannitol, and sorbitol; and sugars such as glucose, fructose, lactose, and sucrose.

The stabilizer is not particularly limited and examples thereof include sugars such as glycerol, mannitol, sorbitol, lactose, and sucrose.

The antioxidant is not particularly limited and examples thereof include ascorbic acid, uric acid, tocopherol homologues (for example, vitamin E, four tocopherol isomers α, β, γ, and δ), cysteine, and EDTA. Stabilizers and antioxidants may be respectively used alone or in combination of two or more thereof.

Examples of the pH adjusting agent include sodium hydroxide, citric acid, acetic acid, triethanolamine, sodium hydrogen phosphate, sodium dihydrogen phosphate, and potassium dihydrogen phosphate.

The pharmaceutical composition may contain an organic solvent, collagen, polyvinyl alcohol, polyvinyl pyrrolidone, a carboxyvinyl polymer, sodium carboxymethyl cellulose, sodium polyacrylate, sodium alginate, water-soluble dextran, sodium carboxymethyl starch, pectin, methyl cellulose, ethyl cellulose, xanthan gum, gum arabic, casein, gelatin, agar, diglycerol, propylene glycol, polyethylene glycol, vaseline, paraffin, stearyl alcohol, stearic acid, human serum albumin (HSA), mannitol, sorbitol, lactose, PBS, sodium chloride, sugars, a biodegradable polymer, a serum-free medium, each of which is pharmaceutically acceptable, or an additive which is acceptable as a pharmaceutical additive.

In particular, in the context of the present invention, the pharmaceutical composition preferably contains ammonium sulfate, L-histidine, purified sucrose, sodium hydroxide, hydrochloric acid, or the like.

The container in which a pharmaceutical composition is filled is not particularly limited, and it is preferably made out of a material having low oxygen permeability. Examples of the container include a plastic container, a glass container, and a bag made out of a laminate film having an aluminium foil, an aluminium-deposited film, an aluminium oxide-deposited film, a silicon oxide-deposited film, a polyvinyl alcohol, an ethylene-vinyl alcohol copolymer, a polyethylene terephthalate, a polyethylene naphthalate, a polyvinylidene chloride, or the like as a gas barrier layer. If necessary, light may be shielded by adopting a bag or the like using a colored glass, an aluminium foil, an aluminium-deposited film, or the like.

In the container in which a pharmaceutical composition is filled, in order to prevent oxidation by oxygen present in the space of the container, it is preferable to replace the gases in the container space and drug solution with inert gases such as nitrogen. For example, an injection solution is bubbled with nitrogen, whereby the filling of the injection solution into a container can be carried out under a nitrogen atmosphere.

The administration method of a pharmaceutical composition is preferably a parenteral administration. For example, intravenous injections such as intravenous drip, intramuscular injection, intraperitoneal injection, subcutaneous injection, intraocular injection, or intrathecal injection may be selected. The specific administration method of a liposome composition includes, for example, a syringe, and administration by intravenous drip.

The dose of a drug contained in the pharmaceutical composition is usually selected from a range of 0.01 mg to 100 mg/kg body weight/day. However, the liposome composition of the present invention is not limited to such a dose.

EXAMPLES

Hereinafter, the present invention will be described in detail with reference to Examples. However, the present invention is not limited to such Examples. The mixing ratio in the solvent composition refers to a volume ratio. For example, "ethanol/ethyl acetate=90/10" refers to 90% ethanol/10% ethyl acetate by a volume ratio.

Example 1 a) Preparation of Emulsification Equipment

The emulsification equipment was prepared by combining a circulation path (the capacity of the circulation path is 6 L) including an intermittent jet flow generating type emulsifying apparatus having a rotating part with a slit outer diameter of 90 mm, an emulsifying tank with a full-water capacity of 26 L, a defoaming tank, and a circulating pump (direct-acting diaphragm pump) as shown in FIG. 1. The capacity of the circulation path is the capacity of the entire circulation path including the defoaming tank.

b) Preparation of Oil Phase

Hydrogenated soybean phosphatidylcholine, cholesterol and N-(carbonyl-methoxypolyethylene glycol 2000)-1,2-distearoyl-sn-glycero-3-phosphoethanolamine sodium salt (hereinafter referred to as DSPE-PEG) were mixed to a molar ratio of 57/38/5, and then an organic solvent (ethanol/ethyl acetate=75/25) was added thereto, followed by warming to 70° C. and dissolution of the lipids to prepare an oil phase. Here, the oil phase was prepared such that the lipid concentration in the oil phase was 70 mmol/L.

c) Preparation of Water Phase 177 mmol/L of an aqueous ammonium sulfate solution was prepared and was then prepared as a water phase in an emulsifying tank.

d) Emulsification

The water phase prepared in c) was heated to 70° C. The oil phase prepared in b) was added so that the volume ratio of water phase/oil phase=8/3 was obtained while operating an emulsifying apparatus at a circumferential speed of 15 m/s and operating a circulation pump at a flow rate of 20 L/min. The total amount of the liquid after the addition was 32 L. After the emulsifying tank was fully hydrated, the overflowed 6 L circulated through the circulation path including the defoaming tank. The internal pressure of the emulsifying tank was set to 30 kPa. In this state, the rotation of the emulsifying apparatus was increased to a circumferential speed of 30 m/sec, followed by stirring for 30 minutes.

e) Desolvation

The organic solvent was removed by ventilating air while heating the emulsion prepared in d) to a temperature higher than or equal to the phase transition temperature of the lipids, thereby producing liposomes.

Example 2

A liposome liquid was prepared in the same manner as in Example 1, except that the circulation pump was operated at a flow rate of 10 L/min.

Example 3

A liposome liquid was prepared in the same manner as in Example 1, except that the circulation pump was operated at a flow rate of 5 L/min.

Comparative Example 1

A liposome liquid was prepared in the same manner as in Example 1, except that the circulation pump was operated at a flow rate of 2.5 L/min.

Comparative Example 2

A liposome liquid was prepared in the same manner as in Example 1, except that the capacity of the emulsifying tank was set to 16 L, the capacity of the circulation path was set to 16 L, and the circulation pump was operated at a flow rate of 12 L/min.

Example 4

A liposome liquid was prepared in the same manner as in Example 1, except that the capacity of the emulsifying tank was set to 16 L, the capacity of the circulation path was set to 16 L, and the circulation pump was operated at a flow rate of 24 L/min.

Example 5

A liposome liquid was prepared in the same manner as in Example 1, except that the capacity of the emulsifying tank was set to 6 L, the capacity of the circulation path was set to 26 L, and the circulation pump was operated at a flow rate of 32 L/min.

Example 6

A liposome liquid was prepared in the same manner as in Example 1, except that the internal pressure of the emulsifying tank was set at an atmospheric pressure and the circulation pump was operated at a flow rate of 10 L/min.

Example 7

A liposome liquid was prepared in the same manner as in Example 1, except that the capacity of the emulsifying tank was set to 20.8 L, the capacity of the circulation path was set to 11.2 L, the liquid volume in the emulsifying tank was set to 80% by volume, and the circulation pump was operated at a flow rate of 14 L/min.

Example 8

A liposome liquid was prepared in the same manner as in Example 1, except that the circulating pump was changed to a rotary pump.

(Measurement of Average Particle Size of Liposomes by Dynamic Light Scattering Method)

The liposome liquids prepared in Examples 1 to 7 and Comparative Example 1 were 40-fold diluted with pure water to obtain samples for measuring an average particle size. The average particle size of the samples for measuring an average particle size was measured in terms of volume average particle size using a particle size analyzer FPAR-1000AS (manufactured by Otsuka Electronics Co., Ltd.). The measurement results are shown in Table 1. Ratings were given as follows: A: average particle size of 55 nm or less; B: average particle size of 56 nm or more and 60 nm or less; and C: average particle size of 61 nm or more.

TABLE 1

| | Emulsifying tank L | Circulation path L | Total L | Liquid volume in emulsifying tank (volume ratio) | Emulsifying tank internal pressure | Circulation flow rate, L/min | Circulation time (min) | Circulation path/whole ratio | Average particle size, nm | Evaluation |
|---|---|---|---|---|---|---|---|---|---|---|
| Example 1 | 26 | 6 | 32 | Full water level (100%) | 30 kPa | 20 | 0.30 | 0.19 | 53 | A |
| Example 2 | 26 | 6 | 32 | Full water level (100%) | 30 kPa | 10 | 0.60 | 0.19 | 55 | A |
| Example 3 | 26 | 6 | 32 | Full water level (100%) | 30 kPa | 5 | 1.20 | 0.19 | 57 | B |
| Comparative Example 1 | 26 | 6 | 32 | Full water level (100%) | 30 kPa | 2.5 | 2.40 | 0.19 | 66 | C |
| Comparative Example 2 | 16 | 16 | 32 | Full water level (100%) | 30 kPa | 12 | 1.33 | 0.50 | 65 | C |
| Example 4 | 16 | 16 | 32 | Full water level (100%) | 30 kPa | 24 | 0.67 | 0.50 | 56 | B |
| Example 5 | 6 | 26 | 32 | Full water level (100%) | 30 kPa | 32 | 0.81 | 0.81 | 58 | B |
| Example 6 | 26 | 6 | 32 | Full water level (100%) | Atmospheric pressure | 10 | 0.60 | 0.19 | 57 | B |
| Example 7 | 20.8 | 11.2 | 32 | 80% | 30 kPa | 14 | 0.80 | 0.35 | 60 | B |
| Example 8 | 26 | 6 | 32 | Full water level (100%) | 30 kPa | 20 | 0.30 | 0.19 | 53 | A |

As can be seen from Table 1, a small average particle size could be attained in Examples 1 to 7, which satisfy the conditions in which the ratio of the capacity of the circulation path to the total capacity of the emulsifying tank and the circulation path is 0.4 or less and/or the circulation time (the time required for the liquid to return to the emulsifying tank after being discharged therefrom) is within 2.0 minutes, whereas a small average particle size could not be attained in Comparative Example 1, which does not satisfy the above conditions.

(Preparation of Drug-Encapsulated Liposomes)

With respect to the non-drug encapsulated liposomes prepared in Example 1, the lipid concentration of the liposome liquid was concentrated to a range of 120 to 150 mmol/L by tangential flow filtration, while the outer water phase of the liposome was replaced with a 0.09 mass % aqueous sodium chloride solution. A drug solution prepared by heating to dissolve gemcitabine hydrochloride in a phosphate buffer solution was added thereto. The mixture was heated at about 70° C. for 30 minutes and then cooled to room temperature. Thereafter, the drug liposome mixture was filtered through a sterilization filter having a pore size of 0.2 μm. Further, the drug liposome mixture was purified by dialysis against a 9.4 mass % sucrose/10 mmol/L-histidine aqueous solution by tangential flow filtration to remove non-encapsulated gemcitabine. This was followed by filtration of liposomes through a sterilizing filter having a pore size of 0.2 μm to obtain a solution of sterile gemcitabine-encapsulated liposomes having an average particle size of 65 nm. According to the present invention, it was confirmed that liposomes having a single dispersion peak and a small average particle size of 100 nm or less usable for medical applications can be produced. Although the average particle size of liposomes described in Evaluation of Table 1 is measured for empty liposomes, if the average particle size of drug-encapsulated liposomes is 100 nm or less, such liposomes can be used for medical use, with the average particle size of 65 nm being a good result.

INDUSTRIAL APPLICABILITY

According to the present invention, miniaturized liposomes can be produced on large scale production. The liposomes produced by the present invention can be applied to medicines, cosmetics, foods, or the like, and are particularly useful for medical applications.

EXPLANATION OF REFERENCES

1: first tank
2: circulation path
3: emulsifying apparatus
4: second tank
5: pump

What is claimed is:

1. An apparatus for producing a liposome, comprising:
a first tank comprising an emulsifying apparatus;
a circulation path;
a second tank in the middle of the circulation path; and
a pump in the middle of the circulation path,
wherein the pump is configured to satisfy the formula "2X≥Y," wherein X refers to the liquid feeding capacity (L/min) of the pump and Y refers to the capacity of circulation path (L),
wherein the first tank and the emulsifying apparatus are configured to stir and emulsify a liquid,
wherein the second tank is configured to separate and remove bubbles which are formed in the first tank,
wherein the ratio of the capacity of the circulation path to the total capacity of the first tank comprising the emulsifying apparatus and the circulation path is 0.4 or less, and said capacity of the circulation path refers to the capacity of the entire circulation path including the second tank,
wherein the pump is placed after the second tank and before the first tank.

2. The apparatus for producing a liposome according to claim 1, wherein the pump is a diaphragm pump or a rotary pump.

3. The apparatus for producing a liposome according to claim 1, wherein an intermittent jet flow generating type emulsifying apparatus is installed in the first tank.

4. The apparatus for producing a liposome according to claim 1, wherein the ratio of the capacity of the circulation path to the total capacity of the first tank and the circulation path is 0.2 or less.

5. The apparatus for producing a liposome according to claim 1, further comprising a mechanism for loading pressure in the first tank.

6. The apparatus for producing a liposome according to claim 2, further comprising a mechanism for loading pressure in the first tank.

7. The apparatus for producing a liposome according to claim 3, further comprising a mechanism for loading pressure in the first tank.

8. The apparatus for producing a liposome according to claim 4, further comprising a mechanism for loading pressure in the first tank.

9. The apparatus for producing a liposome according to claim 1, wherein the ratio of the capacity of the circulation path to the total capacity of the first tank comprising the emulsifying apparatus and the circulation path is 0.3 or less.

10. The apparatus for producing a liposome according to claim 1, wherein the pump is configured to satisfy the formula "X≥Y," wherein X refers to the liquid feeding capacity (L/min) of the pump and Y refers to the capacity of circulation path (L).

11. An apparatus for producing a liposome, comprising:
a first tank comprising an emulsifying apparatus;
a circulation path;
a second tank in the middle of the circulation path; and
a pump in the middle of the circulation path,
wherein the first tank and the emulsifying apparatus are configured to stir and emulsify a liquid,
wherein the second tank is configured to separate and remove bubbles which are formed in the first tank by communication of the circulation path with an outlet at the bottom of the second tank,
wherein the ratio of the capacity of the circulation path to the total capacity of the first tank comprising the emulsifying apparatus and the circulation path is 0.4 or less, and said capacity of the circulation path refers to the capacity of the entire circulation path including the second tank,
wherein the pump is placed after the second tank and before the first tank.

* * * * *